(12) United States Patent
Drucker et al.

(10) Patent No.: US 6,292,796 B1
(45) Date of Patent: *Sep. 18, 2001

(54) METHOD AND APPARATUS FOR IMPROVING ACCESS TO LITERATURE

(75) Inventors: Ernest Drucker, New York; Jonathan D. Meyer, Mt. Vernon; Thomas McGinn, New York, all of NY (US)

(73) Assignee: Clinical Focus, Inc., Mt. Vernon, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/256,966

(22) Filed: Feb. 23, 1999

(51) Int. Cl.[7] ...................................... G06F 17/30

(52) U.S. Cl. .................... 707/5; 707/2; 707/3; 707/6; 707/10; 707/102; 707/513; 707/532; 704/9; 705/27; 705/30; 709/218; 709/219

(58) Field of Search .................... 707/2, 3, 10, 102, 707/5, 6, 513, 532, 1, 9; 705/27, 30; 704/9; 709/218, 219, 226, 227

(56) References Cited

U.S. PATENT DOCUMENTS

| | | | |
|---|---|---|---|
| 5,355,497 | * | 10/1994 | Cohen-Levy .................... 707/200 |
| 5,404,514 | * | 4/1995 | Kageneck et al. ............... 707/5 |
| 5,495,600 | * | 2/1996 | Terry et al. ..................... 707/3 |
| 5,694,592 | * | 12/1997 | Driscoll .......................... 707/3 |
| 5,873,076 | * | 2/1999 | Barr et al. ....................... 707/3 |

(List continued on next page.)

OTHER PUBLICATIONS

Schreiber F A et al: "Dynamic User Profiles and Flexible Queries in Office Document Retrieval Systems" Deceision Support Systems, NL, Elsevier Science Publishers, Amsterdam, vol. 5, No. 1, Jan. 1, 1989 (1989–01–01), pp. 13–28, XP000569991 ISSN: 0167–9236 p. 13, left–hand column, line 1—p. 16, right–hand column, line 50; figures 1,2.

Pazzani M et al: "Learning From Hotlists and Coldlists: Towards a WWW Information Filtering and Seeking Agent" Proceedings, International Conference on Tools with Artificial Intelligence, US, Los Alamitos, CA., Jan. 1, 1995 (1995–01–01), pp. 492–495, XP000567438, p. 492, lefthand column, line 1–p. 493, right–hand column, line 13; figure 1.

(List continued on next page.)

Primary Examiner—Hosain T. Alam
Assistant Examiner—Shanid Alam
(74) Attorney, Agent, or Firm—The Hecker Law Group

(57) ABSTRACT

A method and apparatus for improving access to literature is described. Embodiments of the invention comprise an access mechanism that searches current and past literature (e.g., journal publications or other articles) and selects some or all of the literature for a user based on criteria established for the user. In one embodiment of the invention, the access mechanism is coupled to an electronic medical records system used to enter patient information and user profile information and coupled to one or more literature (e.g., medical, scientific, current affairs, law, dental, etc.) libraries or database(s). Search criteria is obtained from user profile information established for a physician (or other user of the electronic medical records system) and patient information. The search criteria is used to generate a request for literature from the libraries. The search criteria may act as a filter of the literature that is contained in a library. In addition, the results of the request obtained from a library may be filtered based on criteria established for the user. The user may view, save, and/or print the results.

40 Claims, 14 Drawing Sheets

U.S. PATENT DOCUMENTS

| | | | | |
|---|---|---|---|---|
| 5,893,092 | * | 4/1999 | Driscoll | 707/5 |
| 5,911,139 | * | 6/1999 | Jain et al. | 707/3 |
| 5,913,205 | * | 6/1999 | Jain et al. | 707/2 |
| 5,926,812 | * | 7/1999 | Hilsenrath et al. | 707/5 |
| 5,963,940 | * | 10/1999 | Liddy et al. | 707/5 |
| 5,974,412 | * | 10/1999 | Hazlehurst et al. | 707/3 |
| 5,987,457 | * | 11/1999 | Ballard | 707/5 |
| 6,006,225 | * | 12/1999 | Bowman et al. | 707/5 |
| 6,029,161 | * | 2/2000 | Lang et al. | 707/1 |
| 6,029,165 | * | 2/2000 | Gable | 707/3 |
| 6,067,552 | * | 5/2000 | Yu | 707/501 |
| 6,101,537 | * | 8/2000 | Edelstein et al. | 709/219 |

OTHER PUBLICATIONS

Morita M et al: "Information Filtering Based on User Behavior Analysis and Best Match Text Retrieval" Proceedings of the Annual International ACM–SIGIR Conference on Research and Development in Information Retrieval, DE, Berlin, Springer, vol. CONF. 17, 1994, pp. 272–281, XP000475327, p. 272, line 1 –page 274, line 50; figure 1.

Database Inspec Online! Institution of Electrical Engineers, Stevenage, GB; Inspec No. AN26754, XP002140862 abstract & Barkla J.K.: "The University of Sheffield Biomedical Information Project" Information Scientist, vol. 3, No. 1, Mar. 1969 (1969–03), pp. 13–27, UK.

Binkley J et al: "Rama: An Architecture for Internet Information Filtering" Journal of Intelligent Information Systems: Artificial Intelligence and Database Technologies, NL, Kluwer Academic Publishers, Amsterdam, vol. 5, No. 2, Sep. 1, 1995 (1995–09–01), pp. 81–99, XP00061768 ISSN: 0925–9902 p. 81, line 1 –p. 83, line 16.

DIALOG Pocket Guide, 1995 Knight–Ridder Information, Inc., 2440 El Camino Real, Mount View, California 94040, Registered U.S. Patent and Trademark Office #067012, Oct. 1995.*

Ball et al., "An Internet Difference Engine and its applications," AT &T Bell Labs., NJ., Technologies for the Information Superhighway Digest of papers Compcon 1996, ISBN: 0–8186–7414–8, Feb. 25–28, 1996, pp. 71–76.*

* cited by examiner

FIGURE 1

| GEORGIA GENERAL HOSPITAL | | STELLA GLEASON, M.D. | | | CREATED: MARCH 22, 2000 |
|---|---|---|---|---|---|
| Record Number | MMC002320474649 | | Street Address | 300 8th Ave, #18 | |
| Last Name | Stevenson | | | City | Columbus |
| First Name | Margaret | | | State | Georgia |
| Dob | 8/18/48 | | | Zip | 31901 |
| Identifier | 188382367 | | | | |
| Payor Information | | Visit Date | March 22, 2000 | Onset Data | March 18, 2000 |
| 1° Carrier | BC | Active Problem | Hypertension, allegies | Age | 15 |
| Policy Number | YLB188382367 | Subjective | Fever, clear rhinorrhea | History | |
| InsuredParty | Phillip Stevenson | Objective | | | |
| 2° Carrier | | GEN | Appears ill | | |
| Policy Number | | HEENT | inflamed pharynx, TM's normal, PERLA, conjunctiva WNL | | |
| Insured Party | | NECK | Tender anterior cervical adenopathy | | |
| Notes | | LUNGS | Clear to ausculation, equal BS | Lab Results | |
| | | HEART | RR & R, no murmur, gallop, or rub, Not enlarged | | |
| | | ABD | Soft | | |
| | | GENT | | | |
| | | BJE | Mild diffuse muscle tenderness | | |
| | | NEURO | Alert, no meningeal signs | Radiology | |
| | | SKIN | No rashes. No lesions | | |
| | | STUDIES | | | |
| | 1° Diagnosis | INFLUENZA | | 2° Diagnosis | |
| | Plan | Acetominophen, bedrest, fluids until fever free | | Plan | |
| | Medications | Flumadinegeneric-Rimantidine 100 mg. BID | | Medications | |
| | Follow-up | Return if problem worsens or if not better in 1 week | | Follow-up | |

*FIGURE 13*

METHOD AND APPARATUS FOR IMPROVING ACCESS TO LITERATURE

BACKGROUND OF THE INVENTION

1. Field of the Invention

This invention relates accessing and filtering libraries of literature via a computer system.

2. Background Art

Doctors, clinicians, scientists, and other medical professionals consult journal articles for a variety of reasons. For example, a doctor might want to learn more about a certain type of illness or to try to determine how to handle a patient with an unfamiliar set of symptoms. A scientist may wish to discover what other scientists think of a particular theory or treatment regime. Journal articles provide both the doctor and the scientist with a way to find such information. Articles discussing the results of a clinical trial or the side effects of a new drug, for example, can also be found in such journals. If a new method for diagnosing a certain ailment is discovered journals such as the New England Journal of Medicine may decide to publish one or more articles describing how to perform the new method.

Practicing physicians (as well other professionals or individuals) have significant constraints placed on their time. The structure of modern medical practices and the productivity pressures of managed care have circumscribed the time available to keep abreast of recent advances in the medical literature. There are a significant number of new articles that appear on a regular basis from many different sources. It is impossible for a physician to be able to peruse each of the journals and other literature sources to find those articles that are most relevant to the physician's practice or otherwise of interest to the physician.

To obtain articles that discuss issues such as those identified above a person may utilize the Internet. The Internet is an amalgamation of interconnected computer networks that provides anybody who is connected with access to other computers that are also connected to the Internet. The Internet contains a number of searchable data repositories that contain articles related to the medical field. The National Library of Medicine (NLM), for example, provides users with access to a number of different databases via a program called the Internet Grateful Med (IGM). The IGM is accessible via the World Wide Web (WWW). The WWW is a part of the Internet that may be accessed by using a browser application. Netscape Communicator and Microsoft Internet Explorer are examples of several widely used browser applications. The IGM provides access to MEDLINE, a database which contains more than nine million articles from journals throughout the world, and 14 other databases. AIDSLINE, AIDSDRUGS, AIDSTRIALS, DIRLINE, HealthSTAR, HSRPROJ, HISTLINE, OLDMEDLINE, SDILINE, SPACELNE, BIOETHICSLINE, POPLINE, TOXLINE and ChemID, for example, are all available using the IGM.

A problem with using search interfaces such as the IGM is that it requires a substantial amount of time to locate relevant articles. Time to search through databases for articles relevant to a particular subject is not a luxury many medical professionals can afford. Moreover, even if a person does manage to find the time to conduct a search, the articles are not provided at a time when they are immediately pertinent. For example, current systems do not provide a mechanism for providing articles to a doctor when the doctor is seeing patients.

When a doctor sees a patient, information about that patient is typically entered into a medical chart. The medical chart becomes part of the patient's permanent medical history. In some instances the patient's medical chart is in electronic form. Electronic medical records provide doctors and other medical professionals with a simple way to store and retrieve information about a patient. The HBOC in Atlanta Ga. and the SMS in Malvern, Pa. for example are both companies that provide and maintain electronic medical record systems. Current electronic medical record systems do not, however, provide a way for the doctor to obtain journal articles about a particular subject by automatically pulling information directly from the patient's medical chart and querying a medical library for information about that subject. In the prior art, the patient's medical chart is separate from journal article retrieval systems such as the IGM.

If a doctor wants to conduct a search of a medical journal database using a particular patient's information, the doctor must manually decide what information is pertinent, create a query using that information using the appropriate query format for the database and submit that query to a search program. If the doctor then becomes curious about the side effects that might occur if a certain type of drug is used to treat that patient then the doctor must manually create another search and submit it to the search program. This process can become laborious and has the negative effect of discouraging doctors or any other person who has a need for such articles from searching for them. To understand other problems associated with existing search techniques it is helpful to examine the current methods used to query medical libraries.

The IGM, for example, is capable of processing queries for information in several different ways. A detailed illustration of these query methods and the problems associated with them follows. Referring now to FIG. 1 an interface for querying MEDLINE is shown. There is a row of action buttons 100–104 across the top of the interface. Each action button performs a different function. Below the action buttons 100–104 is a section 110 for entering query terms. Section 110 contains three empty text boxes 111–113. Words or phrases to search on may be entered into text boxes 111–113. Whatever is entered into the text boxes 111–113 can be searched using three methods. The method is selected using pull-down boxes 114–116. Pull-down box 114, for example, contains the options subject, author name, or title word. If author name is selected the search program will use the information entered into text box 111 to search for articles written by a certain author. The default state for pull-down boxes 114–116 is to conduct a subject search.

Once a query term is entered in text boxes 111–113 the search may be performed. To perform a search the user selects action box 100. Once a query is submitted all the records that match the parameters entered in text boxes 111–113 are retrieved. For example, if a doctor enters the words "Alzheimer's Disease" into text box 112 and clicks on action button 100 a list of articles that mention Alzheimer's Disease is displayed. If the doctor conducts the same search at a later date a list of all the articles previously located and any new articles entered into the database since the last search is displayed.

If the amount of results retrieved by the search is excessively large limits can be placed on the search. Section 120 is utilized to apply limits. Limits enable the user to narrow the amount of information being retrieved using a certain set of query terms. Section 120 contains a number of different limit boxes 121–128. Each limit box allows the user to place a different kind of limit on a search. For example, the user can elect to only search for articles between two dates by entering a begin date in limit box 124 and an end date in limit box 128. Limit box 121 allows the user to retrieve articles written in a particular language. Limit box 122 provides the user with a way to specify whether the articles retrieved contain data that was the result of studying humans or animals. Limit box 123 allows the user to identify an age group while limit box 126 allows the user to specify a gender to search for. Limit box 127 and limit box 125 provide a way to control the type of articles retrieved during a search. Limit box 125, for example, allows the user to specify what type of publications to search. If a user wants only to obtain articles about clinical trials the user could specify that using limit box 125. Additionally, action box 103 may be utilized to select what journals to specify in limit box 127.

Existing limiting systems do not provide a way to organize or categorize the results obtained from the search according to user defined criteria. For example, there is no way for a user to prevent a particular article from being retrieved if the user has already read that article. Furthermore, search terms and limits must be manually entered every time a new search is conducted. In the prior art, users cannot specify a set of parameters and then automatically apply those parameters to every search that is conducted. For example, a user cannot direct the search program to pull information from a patient's medical record and search for articles about that information.

Referring now to FIG. 2 a results screen is shown. When a search is performed the user is displayed the results screen. The results screen contains a list 210 of articles matching the search criteria specified by the user. At the top of the results screen is a number of action buttons 200–203. Each action button performs a different function. Action button 200, for example, obtains a long record for all the documents recovered during the search. Action button 201 allows the user to download a document to disk. Action button 202 allows the user to order documents and action button 203 returns the user to the initial search screen shown in FIG. 1.

Below action buttons 200–203 is a list 210 containing citations that matched the search query entered by the user. A short record 211–214 represents a shortened version of each citation. How many short records 211–214 are displayed depends upon the scope of the search. A problem with results screens is that an excessive number of references may be displayed. FIG. 2, for example, shows four short records 211–214 of the five hundred and four retrieved. In operation the number of articles retrieved may be even larger. Users often lack the time to sufficiently peruse all of the displayed references at the time of retrieval. To the left of each short record 211–214 is a full citation button 216, and a related articles button 217. When the related articles button 217 is depressed a new display of citations conceptually related to the first one will appear. The user can go several levels deep and by clicking the related articles button 217 multiple times can obtain numerous lists of articles that are conceptually related to one another. When the full citation button 216 is depressed, the long record for the adjacent citation is displayed. FIG. 3 shows an example of a long record. In some instances, the long record contains an abstract that briefly summarizes the contents of each article. Citations lacking abstracts are marked "no abstract available" in the short record.

Present search interfaces, such as the one described above, have limited functionality. For example, such systems do not have the ability to filter search results based on a user's prior search history. The user may specify limits for each search, but each time a new search is conducted new search limitations must be entered. It would be beneficial to the user to have a system that enables the user to define a set of user specified search preferences that may be applied to any search the user conducts. It would be of further benefit to the user if these search preferences were correlated with entries in an electronic medical record.

SUMMARY OF THE INVENTION

A method and apparatus for improving access to information is described. Embodiments of the invention comprise an access mechanism that searches current and past literature (e.g., journal publications or other articles) and selects some or all of the literature for a user based on criteria established for the user. In one embodiment of the invention, the access mechanism is coupled to an electronic chart system used to enter patient information and user profile information and coupled to one or more literature (e.g., medical, scientific, current affairs, law, dental, etc.) libraries or database(s). Search criteria is obtained from user profile information established for a physician (or other user of the system) and patient information. The search criteria is used to generate a request for literature from the libraries. The search criteria may act as a filter of the literature that is contained in a library. In addition, the results of the request obtained from a library may be filtered based on criteria established for the user. The user may view, save, and/or print the results.

In one or more embodiments of the invention, the access mechanism comprises a user setup, record link, standing search and ad hoc access components. The user setup allows a user to enter user information (e.g., userid, password, etc.) and identify fields in an electronics medical records system whose values are used as search criteria. Further, the user setup is used to identify the sources (e.g., journals, newspapers, textbooks, etc.) of the information and the time frame in which to search.

Record link, standing search and ad hoc access provide different types of searching. A record link search is coupled to a patient's chart in the electronic medical records system. A search is invoked whenever a user enters the patient's chart. Fields in the patient's chart may be used as search criteria. The user is notified from within the electronic medical records system that new articles were found during the search. An ad hoc access may be performed at any time using information contained in fields of the patient's chart. A user may alter the search criteria specified in user setup. For example, the user may identify different sources and time ranges for performing the search.

A standing search allows the user to perform a search without accessing a patient's chart. The standing search is specified in user setup and is performed periodically as new information becomes available.

BRIEF DESCRIPTION OF THE DRAWINGS

Figure 1:
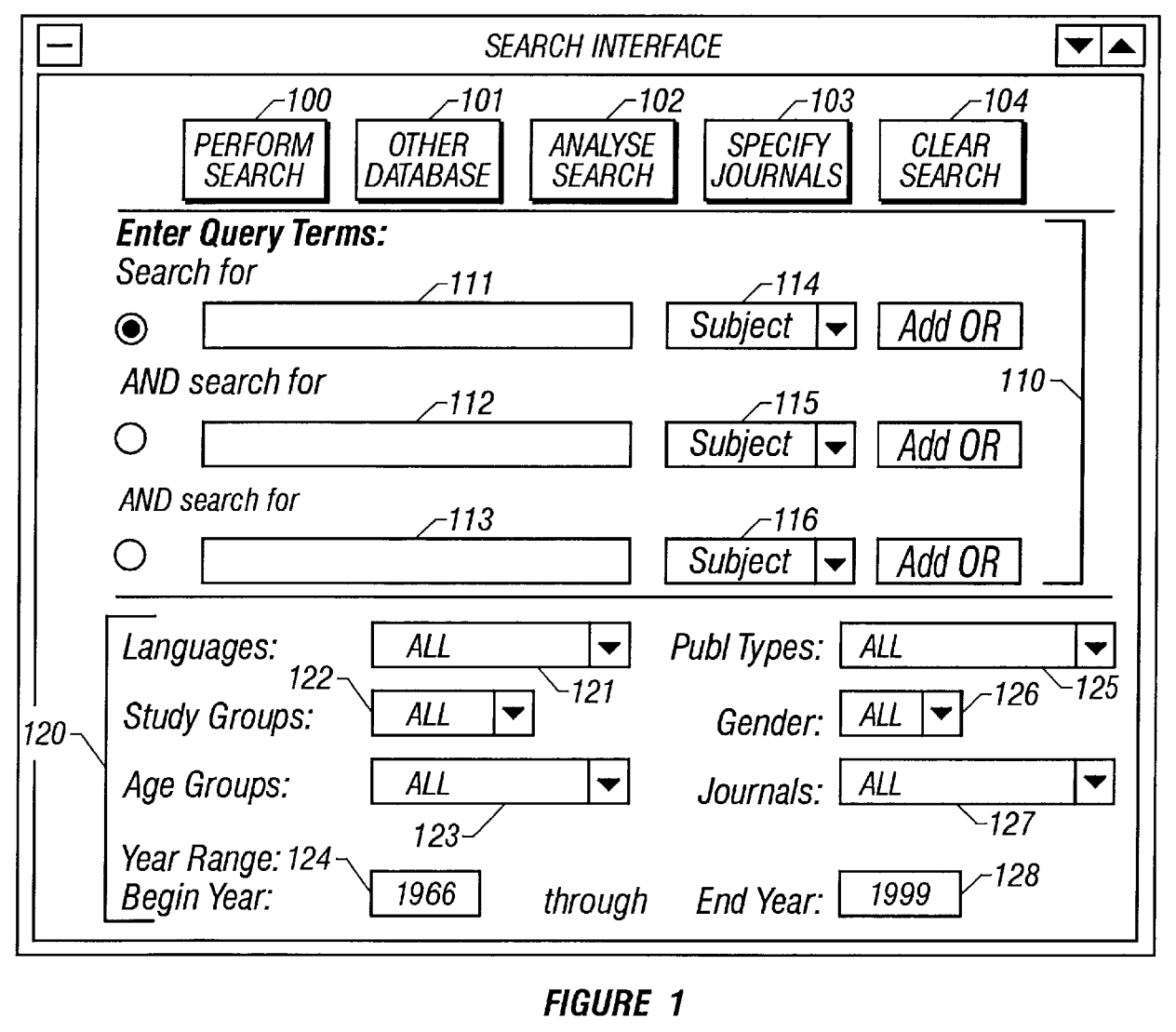

FIG. 1 provides an example of an interface for querying MEDLINE.

FIG. 13 provides an example of a patient chart display according to an embodiment of the invention.

DETAILED DESCRIPTION OF THE INVENTION

Figure 2:
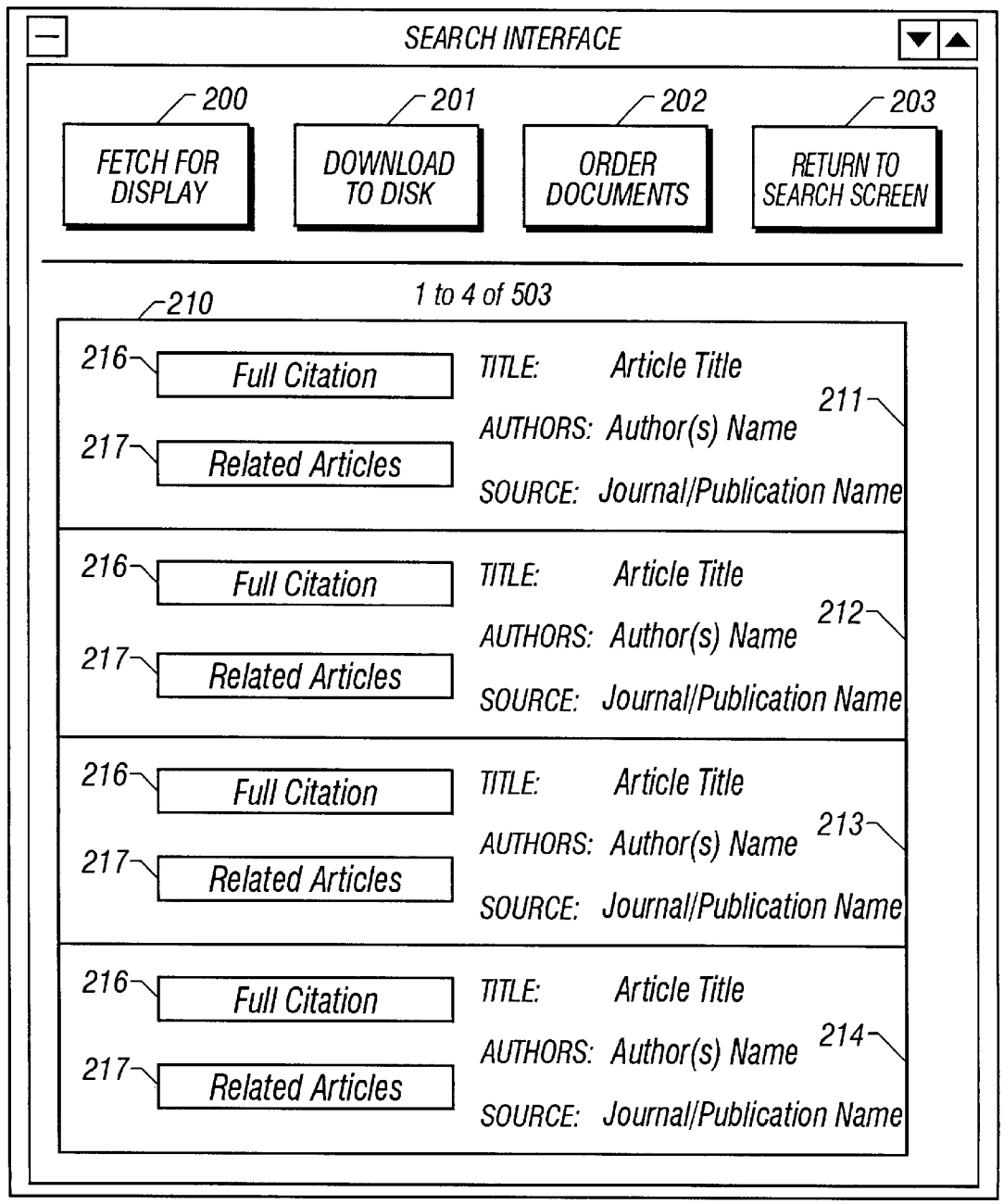
FIG. 2 provides an example of screen containing the results of a MEDLINE search.
Figure 3:
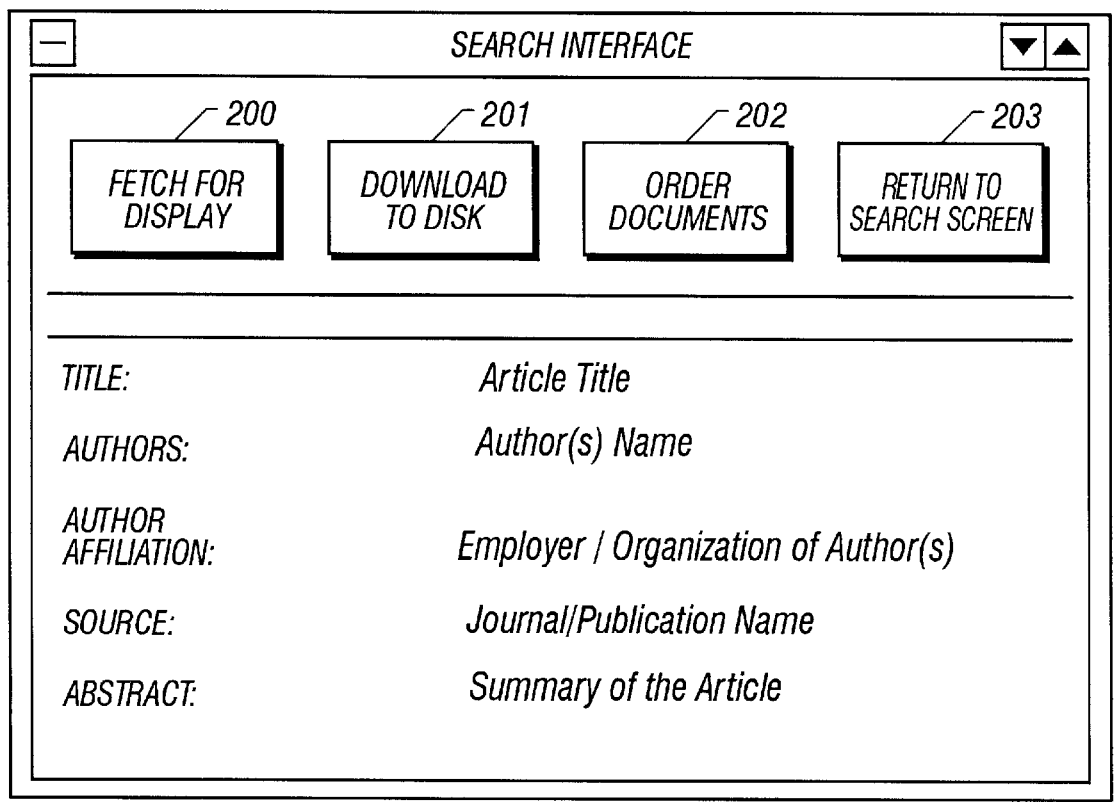
FIG. 3 provides an example of a long record.

A method and apparatus for improving information access is described. In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

A method and apparatus for improving access to information is described. Embodiments of the invention comprise an access mechanism that searches current and past literature (e.g., journal publications or other articles) and selects some or all of the literature for a user based on criteria established for the user. The access mechanism of embodiments of the invention improves prior art access mechanisms such that search criteria may be automatically formulated and results are filtered based on specified interest that may be determined from a user profile, user preferences, and/or search history. Further, in one or more embodiments of the invention in which the access mechanism is coupled to a system of entry (e.g., a patient charting system such as may be used in a medical or dental environment), special criteria may be determined from data entry retrieved from such a coupled system. The user is notified in one or more ways when literature of interest is found.

Embodiments of the invention are described herein with reference to an electronic medical records system. However, it should be apparent that embodiments of the invention may be used with other systems. For example, embodiments of the invention may be used to extract information from a case management system used in the legal field as well as any other system that contains keywords that may be used to search literature libraries and/or databases. Further, embodiments of the invention may be used independent of a such systems to access and filter information.

The access mechanism triggers a literature search at various times. Notification of the results of the search may occur as results are obtained or at a later time. For example, a search may be conducted each time a physician, or other care provider, enters a patient's record in the electronic medical records system. The physician is notified of the status (e.g., whether or not any literature was obtained in the search) of the search within the window displaying the patients record. Alternatively, a search may be conducted independent of access to a patient's record. A search may be conducted at specified time intervals (e.g., on a weekly, daily, and/or as new literature becomes available). Further, a search may be conducted on an ad hoc basis in response to a user's specific request for a search.

Further, search results are filtered in an effort to eliminate literature that is not of interest to the user. A search may be limited to certain sources and dates of the literature. For example, a physician may wish to specify the medical journals, biomedical research journals, medical textbooks, treatment guidelines, newspapers and/or magazines from which literature is identified during a search. Further, the physician may indicate that the search be limited to that literature dated no earlier than six months from the current date of the search. Subsequent searches may be limited to only that literature that has become available since the last search. For example, if a search was conducted in June, a search that is conducted in December of the same year need only retrieve that literature that has become available since the search conducted in June.

Further, the searched literature may be filtered by information extracted from a patient's chart (e.g., diagnosis, age, gender, etc.). The search results may be further filtered to eliminate literature based on a user's search history and preferences. For example, literature that has been found in a previous search and disposed of in some manner need not be included in the results of a subsequent search. The user has the option of viewing, saving, and/or printing an article that has been found in a search, for example. If the physician has already saved the article using a catalogue feature of one or more embodiments of the invention, there is no need to present the same article to the physician unless the user expressly requests the same article.

Filtering of the search results may occur as a result of the criteria used to conduct the search (i.e., during a search) or after a search to eliminate unwanted or unnecessary results, or both during and after a search. The journals and/or time range filters may be specified as part of the search criteria sent to the literature databases or libraries, for example. Filtering based on previous search activities may be performed on the search results received from the literature databases, for example.

In one or more embodiments of the invention, literature that is found in a search may be viewed, saved, printed and/or electronically mailed (i.e., emailed). In an embodiment of the invention, a screen presented to the user provides a menu that included entries that identify the different types of literature (e.g., professional articles, lay literature, practice guidelines, texts, etc.) and the number of articles from each. The user can select one of the menu entries to view the citations for articles in the selected literature category. The user can select one of the citations to view the full text of the article. The user may choose to print, save or email the cited article, or save the entire search results. These options are discussed in more detail below.

Figure 4:
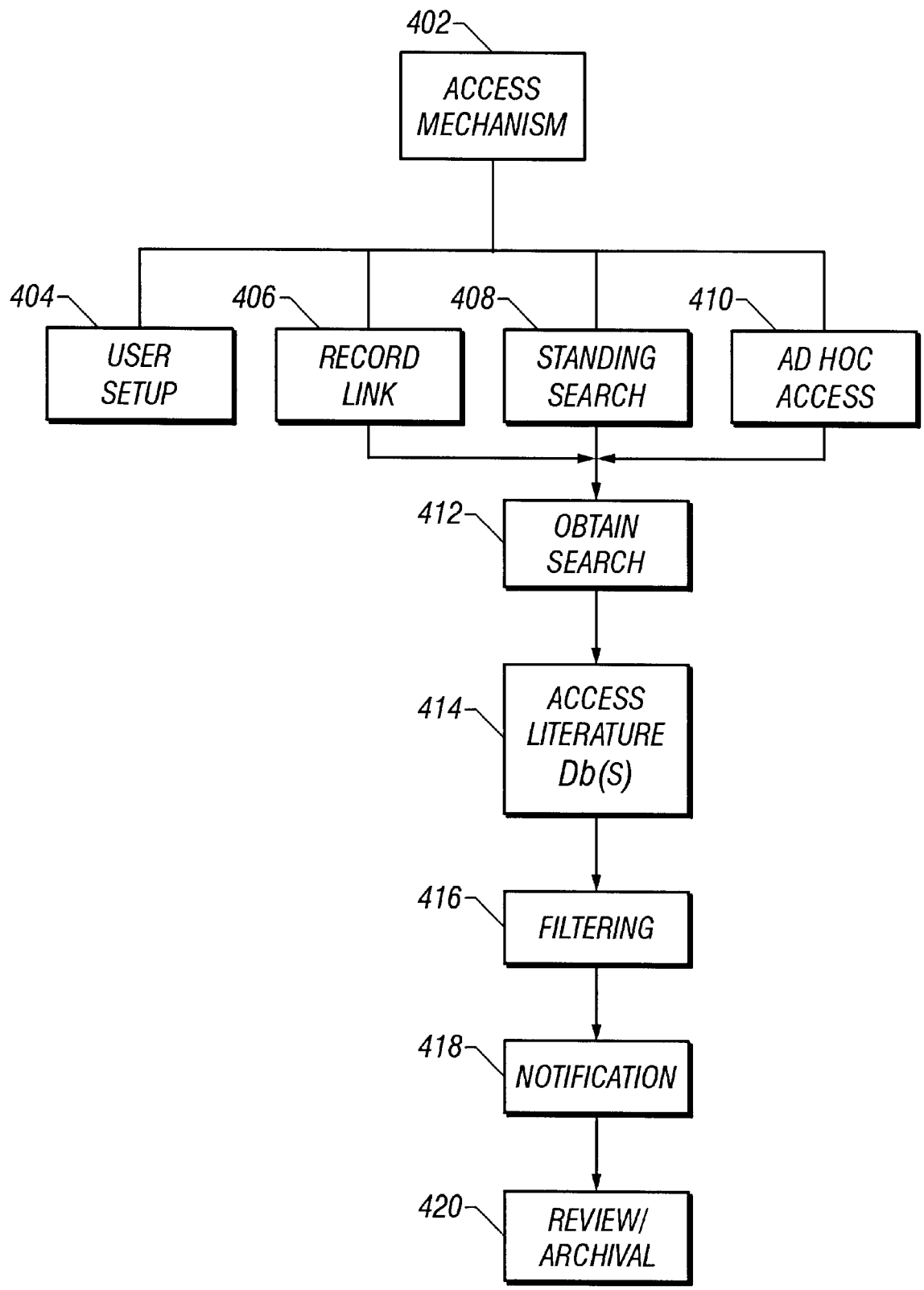
FIG. 4 provides an overview of the access mechanism according to one or more embodiments of the invention.

FIG. 4 provides an overview of the access mechanism according to one or more embodiments of the invention. Access mechanism 402 comprises user setup 404, record link 406, standing search 408 and ad hoc access 410.

In one or more embodiments of the invention, user setup 404 is incorporated into the user setup procedures of the electronic medical records system. In user setup 404, user preferences and profile information is established for a user. For example, the user may specify a unique user identification (i.e., a userid) and password, a practice area or specialty, an institutional affiliation (e.g., a hospital or other place of employment). A user may also specify search preferences such as the type of literature that is to be searched and the time frame of the search. In one embodiment of the invention, one or more medical journals (e.g., New England Journal of Medicine and Journal of the American Medical Association) are identified as default sources that may be overridden. In addition to the default literature sources, one or more journals or other literary sources may be automatically selected based on the physician's practice area or specialty which may be overridden by the user.

The time frame of the search (e.g., last month, six months, year, two years, three years, or no time limit) is used to determine how far back to select literature when performing a search such as a new search or where a search has not been updated for a long period of time. The time limit may be set differently for each source. Further, the time frame may be overridden at any time such as when a search is performed via ad hoc access 410.

Further, the fields of the patient's chart (e.g., primary, secondary, etc.diagnosis fields; patient's gender, age, chief complaint, and symptoms; and history of the present illness) that are to be used as search criteria in a record link 406 search may also be specified in user setup 404. A natural language query (e.g., an English-like search request) may be specified for use in standing search 408. Other types of queries may be used as well. For example, the query specification used in record link 406 and/or ad hoc access 410 may also be used. A structured query language or other query expressions may also be used with embodiments of the invention.

Record link 406 is used in one or more embodiments of the invention to link a system used to enter case information (e.g., an electronic medical records system) with one or more repositories of literature. For example, record link 406 may be used to link data entered for a patient (e.g., chart information) in an electronic medical records system to electronic database or libraries containing medical literature. Record link 406 may be used to access literature related to a patient's diagnosis (e.g., primary, second, tertiary, etc.) entered into the electronic medical records system, for example. The fields specified in user setup 404 as sources for search criteria are extracted from the patient's record and become part of a query to the literature databases. A filtering may be performed on the results of the search such that only the pertinent literature is presented to the physician.

In record link 406, a search is updated each time the user accesses a patient's chart, if necessary. However, a search may also be performed independent of accessing a patient's chart. In standing search 408, for example, a search may be performed periodically. In user setup 404, a user may specify a standing search that is periodically initiated while the standing search is still valid (i.e., not removed). In one or more embodiments of the invention, the user may enter the search request in a natural language (e.g., English-like), or other language. Access mechanism 402 parses the natural language request to retrieve keywords, dates, sources, etc. Initially, the search is performed for the time frame specified in user setup 404 (e.g., publications within the last six months) and periodically thereafter to update the search. For example, the search may be performed on a regular basis (e.g., daily, weekly, monthly, etc.) or as new literature becomes available (a new issue of a journal is published).

Ad hoc access 410 to literature databases may occur via access mechanism 402. That is, a user can at any time enter a query that is used to search the literature databases. The user has the option of modifying the settings established in user setup 404 (e.g., sources to be searched, the time frame of the search, etc.) for an ad hoc search.

Access mechanism 402 may be used to perform filtering of a search. Filtering may be performed using the search criteria specified in user setup 404. In the case of record link 406, standing search 408 and ad hoc access 410 options, the search criteria is obtained at block 412 from values established in user setup 404 (e.g., literature sources, time frame, etc.). Additional criteria is obtained from values of specified field's of a patient's chart in record link 406 and/or ad hoc access 410 search(es). Criteria specified in a natural language search request may be used in standing search 408.

At block 414, a search is performed on the literature database(s) using the search criteria obtained in block 412. At block 416, filtering may be performed on the results of the search request. For example, literature that does not satisfy the journal and time frame specified may be eliminated, if necessary (e.g., if the journal and time frame criteria was not expressed as part of the search). Further, the articles that have already been perused by the user may be removed from the search.

If there is some literature that satisfied the search and filtering, the user is notified that there are search results that may be reviewed at block 418. The type of notification may depend on whether the search was conducted via record link 406, standing search 408 or ad hoc access 410. For example, record link 406 and ad hoc access 410 notifications comprise an alert icon or other status output that appears in one or more display(s) of the electronic medical records system or other display. For example, the color of an icon may reflect whether or not there are search results available for review (e.g., green and red may indicate the availability and unavailability, respectively, of search results). Thus, the physician is notified of the status of a search associated with the patient while viewing the patient's chart. As is described in more detail below, the user may select the icon (e.g., click on the icon) to view the search results without exiting the electronic medical records system.

In one or more embodiments of the invention, a user may specify the type of notification for standing search 408 in user setup 404. For example, a user may be notified via email, a phone call, facsimile, and/or page. Where notification is to made via email, the user may specify the type of information to include, e.g., whether the email should include a brief (e.g., title and author) or detailed (e.g., title, author and abstract) description and the location of the full text. Full text locations may be specified in the form of a uniform resource locator (URL) that specifies the location in a computer system or interconnected system of computers (e.g., the Internet), for example, where the full text may be found. Instead of including a brief and/or full description of an article, the email may contain a series of URLs that identify a path for locating the brief and detailed descriptions as well as the full text. The email may contain bibliographic information (e.g., title, author, publication, date and pages) or a URL for accessing this information.

A phone message may be sent to a preset phone number, for example to a voice mailbox, that alerts the user that there are search results. An email message containing information about the search results as described above may be used as notification. Similarly, search result information may be sent via facsimile to a preset phone number. Like an email message, the facsimile may contain the full text, a brief description and/or full description of each article as well as bibliographic information and/or URLs to locations that contain this information.

The user may choose to receive a pager message as notification. The user may opt to limit the time of day in which a page is sent via user setup 404. The search results may be made available via email, fax or both as specified in user setup 404.

At block 420, the user may review the results of the search and, where desired, archive some or all of the search results. For example, the user may choose to save the full text of an article that is of interest. As described in more detail below, the user may catalogue the article in one or more archival categories such as by journal, by organ system to which the article is related, the type of diagnosis or a user-specified category (e.g., a research project).

Record Link

Figure 5:
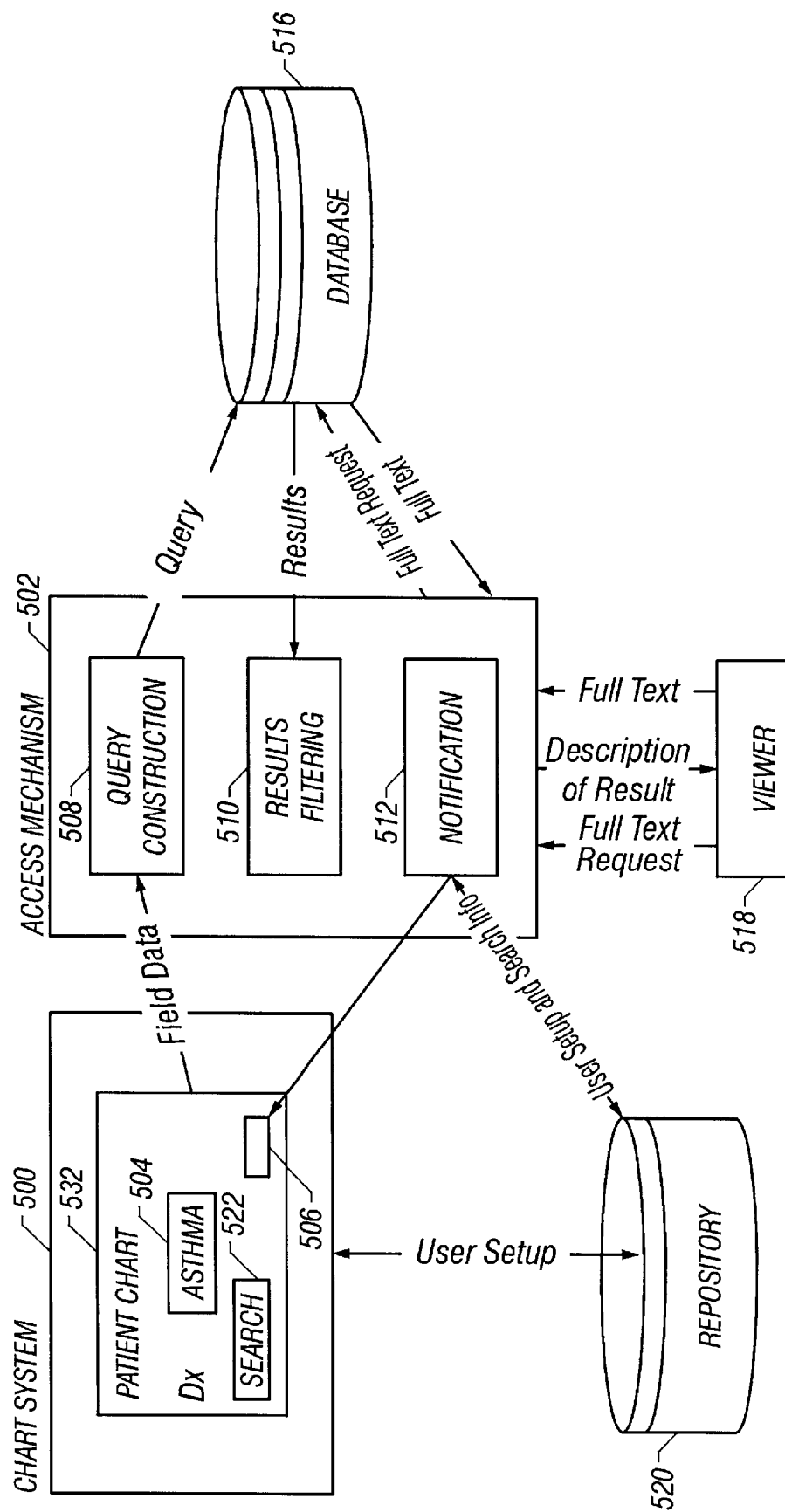
FIG. 5 illustrates a record link search overview according to an embodiment of the invention.

In one or more embodiments of the invention, record link 406 triggers a search as a result of a user accessing a chart within an electronic medical records system. FIG. 5 illustrates a record link search overview according to an embodiment of the invention.

Chart system 500 displays patient chart 532 which contains values of fields identified in user setup 404 for use in a search. Patient chart 532 contains patient information in fields such as a diagnosis field (a more complete example of a patient chart display is provided in FIG. 13). The value contained in fields of patient chart 532 such as diagnosis field 504 (e.g., asthma) may become input to query construction 508 of access mechanism 402. Information contained in repository 520 such as journals to be searched and search time frames entered via user setup 404 may be used in query construction 508.

A query is generated via query construction 508 and forwarded to database 516 that represents one or more searchable libraries or databases. Database 516 is assumed to contain bibliographic information, a brief and/or detailed description, and the full text. A query may search keywords associated with an article, an article's title and/or an article's abstract, for example. It should be apparent that one or more databases may be used to conduct the initial search that do not contain the full text of the articles located during the search. A full text database may be accessed to retrieve the full text of an article selected for retrieval by the user.

The results of the database search are returned to access mechanism 502. Results filtering 510 ensures that those articles that do not satisfy the user setup information are filtered from the search results. For example, only those articles that are published in the sources and time frame specified in the user setup information are kept in the search results. Further, the search results are filtered to remove those articles that have already been presented to the user. Repository 520 contains a search history for each user. In one or more embodiments of the invention, an article that has been presented to the user "n" times (e.g., five or six times) is not presented thereafter. If it is known from the user information contained in repository 520 that the user has already saved the article, the article may be filtered from the search results.

If one or more articles is included in the filtered search results, a notification is sent to the user which is displayed in the form of icon 506. As described above, icon 506 may change color depending on whether or not there are search results available for the user's review.

Access mechanism 402 populates viewer 518 such that the user may review and archive the search results. The user may review a description of the results and request the full text of an article of interest, for example. Access mechanism 402 maintains the URLs (e.g., in repository 520) or other locating information for each article identified in the filtered search results. Thus, upon a request for full text, access mechanism 402 requests the full text from its location (e.g., database 516) and displays the full text in viewer 518.

Figure 6A:
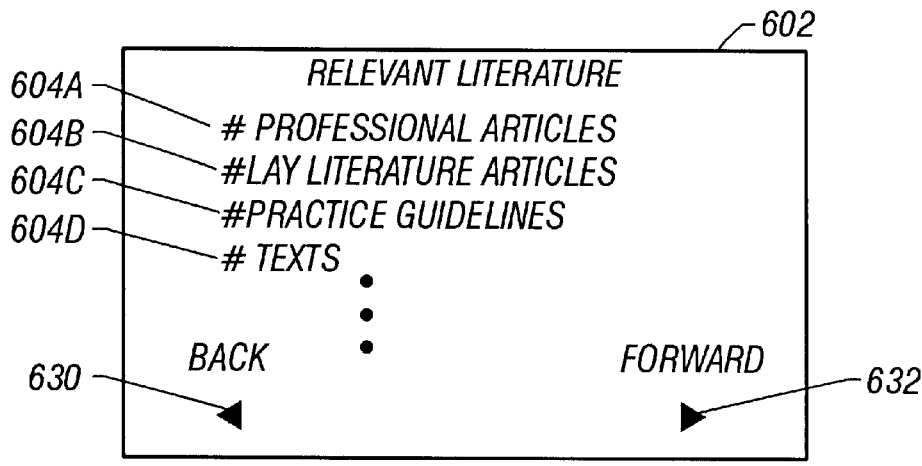
FIGS. 6A–6C provide an example of a review UI according to an embodiment of the invention.
Figure 6B:
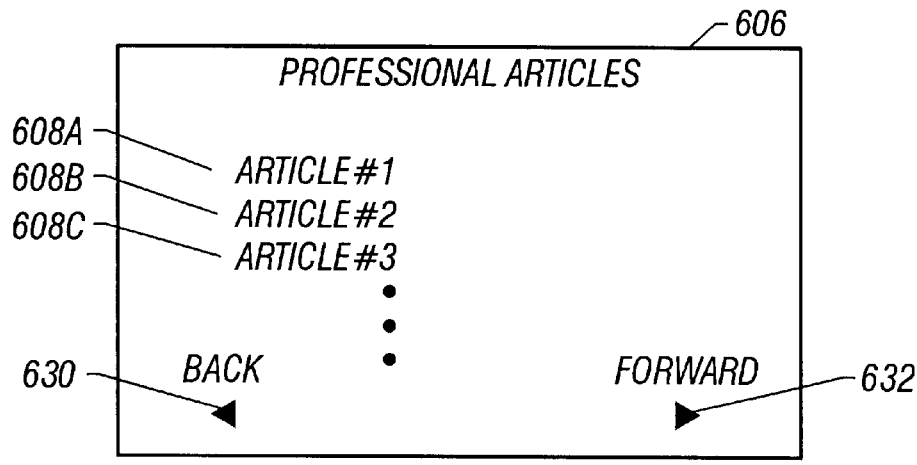
Figure 6C:
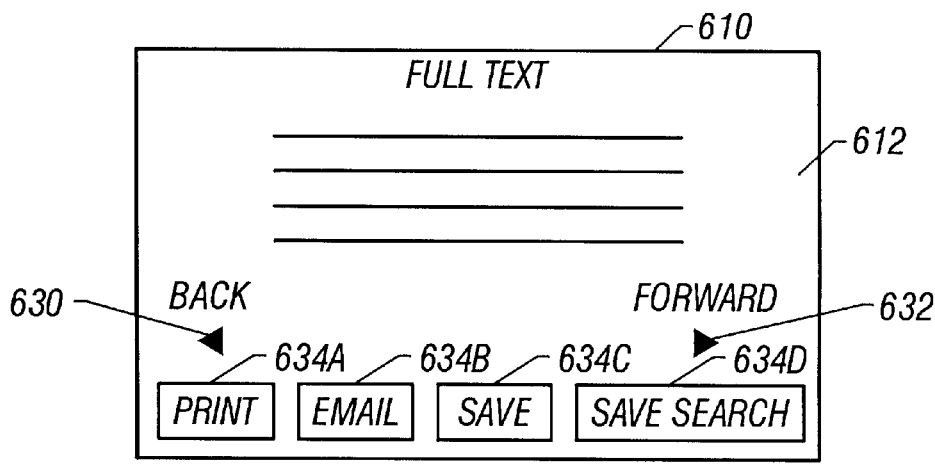

Viewer 518 may comprise one or more displays to present the filtered search results. FIGS. 6A–6C provide an example of a viewer UI according to an embodiment of the invention. If the user chooses to view the filtered results of a search, an embodiment of the invention displays FIG. 6A which provides a summary the types of articles contained in the filtered search results. That is, for example, the number of articles that were found in medical journals are identified in line 604A. Similarly, the number of articles in newspapers and magazines, practice guides and texts are identified in lines 604B–604D. Where the summary is too large to fit in one screen, scrolling icons (e.g., icons 630 and 632) are provided to navigate through the summary screens.

Lines 604A–604D are linked (e.g., hypertext linked) to a detailed display that contains a description of the articles (e.g., title, author, journal, date, pages) in each category. For example, if the user selects line 604A, display 606 of FIG. 6B is viewable (e.g., lines 608A–608C) in which the first "n" articles in the "Professional Articles" category are displayed. Lines 608A–608C are each associated with a given article in the filtered search. The user may scroll through the articles that are contained in the selected category.

The user may select the full text of an article by selecting one of entries (e.g., lines 608A–608C) in display 606. Access mechanism 402 retains a location (e.g., URL) from which the full text of an article contained in the filter search results may be obtained. If the user selects one of lines 608A–608C, access mechanism 402 uses the location information to obtain the full text and display it in display 610 of FIG. 6C. The user may scroll through the full text. Further, the user is presented with the options of printing, emailing or saving the article (i.e., buttons 634A–634C, respectively). The user may also save all of the search results using button 634D.

Using FIGS. 6A–6B a user is able to progress from general information regarding the filtered search results to the full text of a article identified in the filtered search results. Alternatively, prior to viewing the filtered search results, the user may be presented with viewing options such as whether or not the user wishes to see brief descriptions of each article, detailed descriptions of the articles, no description, full text on screen, or the full text printed. If the user selects brief descriptions, FIG. 6B may be displayed. If the user selects detailed descriptions, a modified FIG. 6B is provided that contains the brief description of the articles in addition to the abstracts of the articles. If the user chooses to view no descriptions, the user is asked whether the user wishes to keep the articles for future use, perform a new search, or exit the system. If the user chooses to view the full text of the articles, FIG. 6C may be used to display the full text.

Thus, using record link 406, the user may access relevant information associated with a patient without the need to leave the electronic medical records system and without the need to reenter the information in a search specification screen of an online database.

Figure 7:
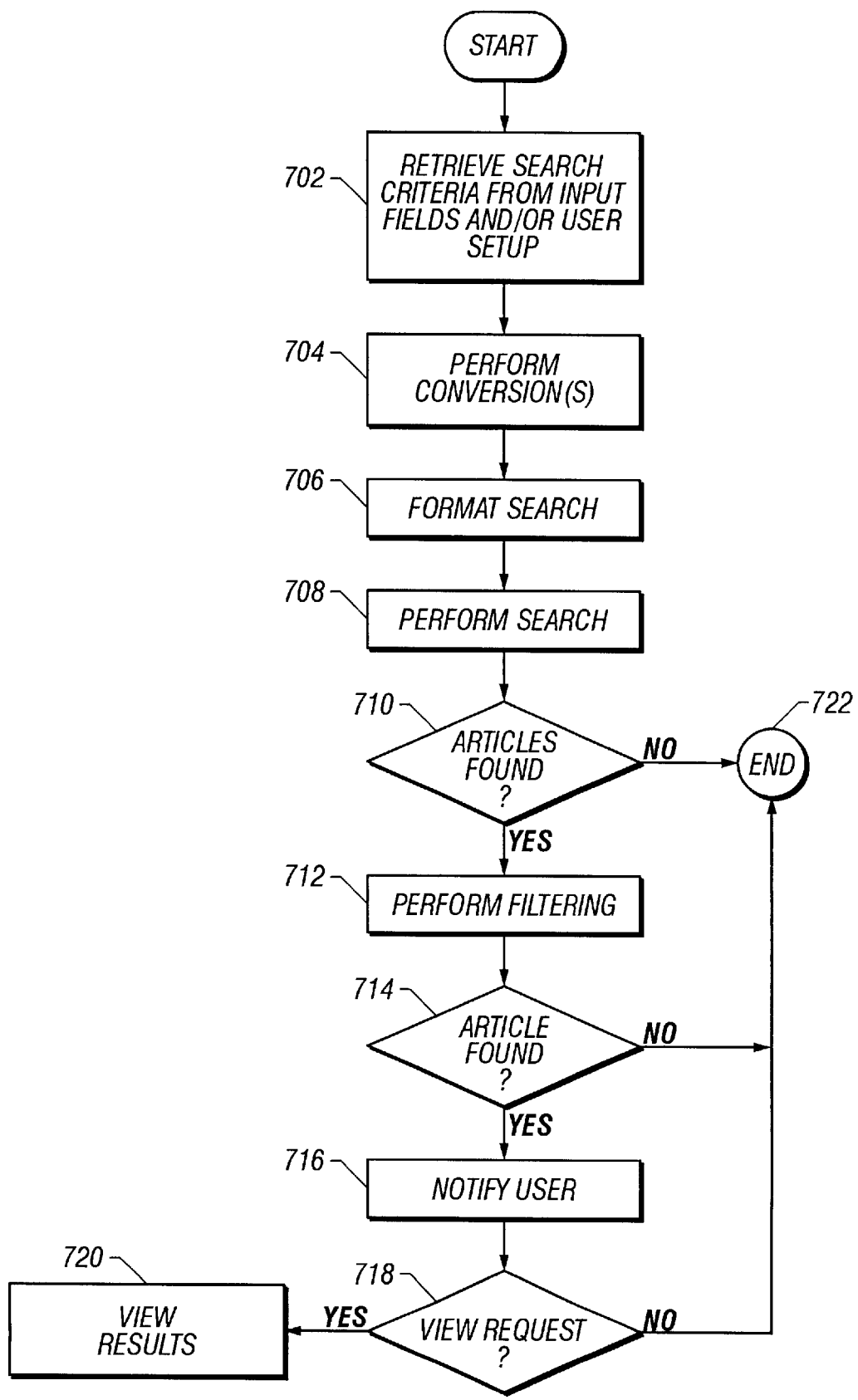
FIG. 7 provides an example of a record link process flow according to an embodiment of the invention.

FIG. 7 provides an example of a record link process flow according to an embodiment of the invention. At step 702, the criteria for the search is obtained from chart fields and from the user's (e.g., the physician accessing the patient's chart) setup information. At step 704, conversions are performed on the chart field values, if necessary. For example, a diagnosis may be expressed in an international classification of disease (ICD) numeric value. A table lookup or other conversion operation may be performed to determine the name equivalent of the ICD value. Both the value and name for a diagnosis may be included in the search. A conversion may be performed on a numeric value of the patient's age to identify an age category (e.g., adult or pediatric).

At step 706, the search request is formatted. Based on information supplied in user setup 404, search criteria may be expressed as alternatives to or as further clarification of other search criteria using operands such as "and" or "or." For example, a user may have specified in user setup 404 that both a primary and secondary diagnosis (if available) are to be used in a search. In this case, the user may specify whether articles are to be identified that are related to both of these diagnoses (i.e., "and") or to either (i.e., "or").

At step 708, the search is performed on database 516. At step 710, a determination is made whether any articles were found in the search. If not, processing ends at step 722. If one or more articles were identified, processing continues at step 712 to filter the search results, if necessary (e.g., articles already known to the user). At step 714, a determination is made whether the filtered search results contain any articles. If not, processing ends at step 722. If so, processing continues at step 716 to notify the user in the manner identified in user setup 404.

If a request is made to review the filtered search results, processing continues at step 720 to provide one or more displays for viewing the search results.

Standing Search

In one or more embodiments of the invention, standing search 408 triggers a search on a periodic basis. A standing search may be entered as a natural language request (e.g., an English language request). For example, a standing search may be:

find information related to asthma published after Dec. 1,1998 in NEJM or JAMA.

The standing search identifies criteria to be used in the search process. The keyword "asthma" is identified as well as a time range (i.e., literature published after Dec. 1, 1998) and the sources of the literature (i.e., the New England Journal of Medicine and the Journal of the American Medical Association). The standing search is parsed to extract the criteria which is presented to the user for approval. A standing search is periodically used to search database 516 for literature that satisfies the standing search.

Figure 8:
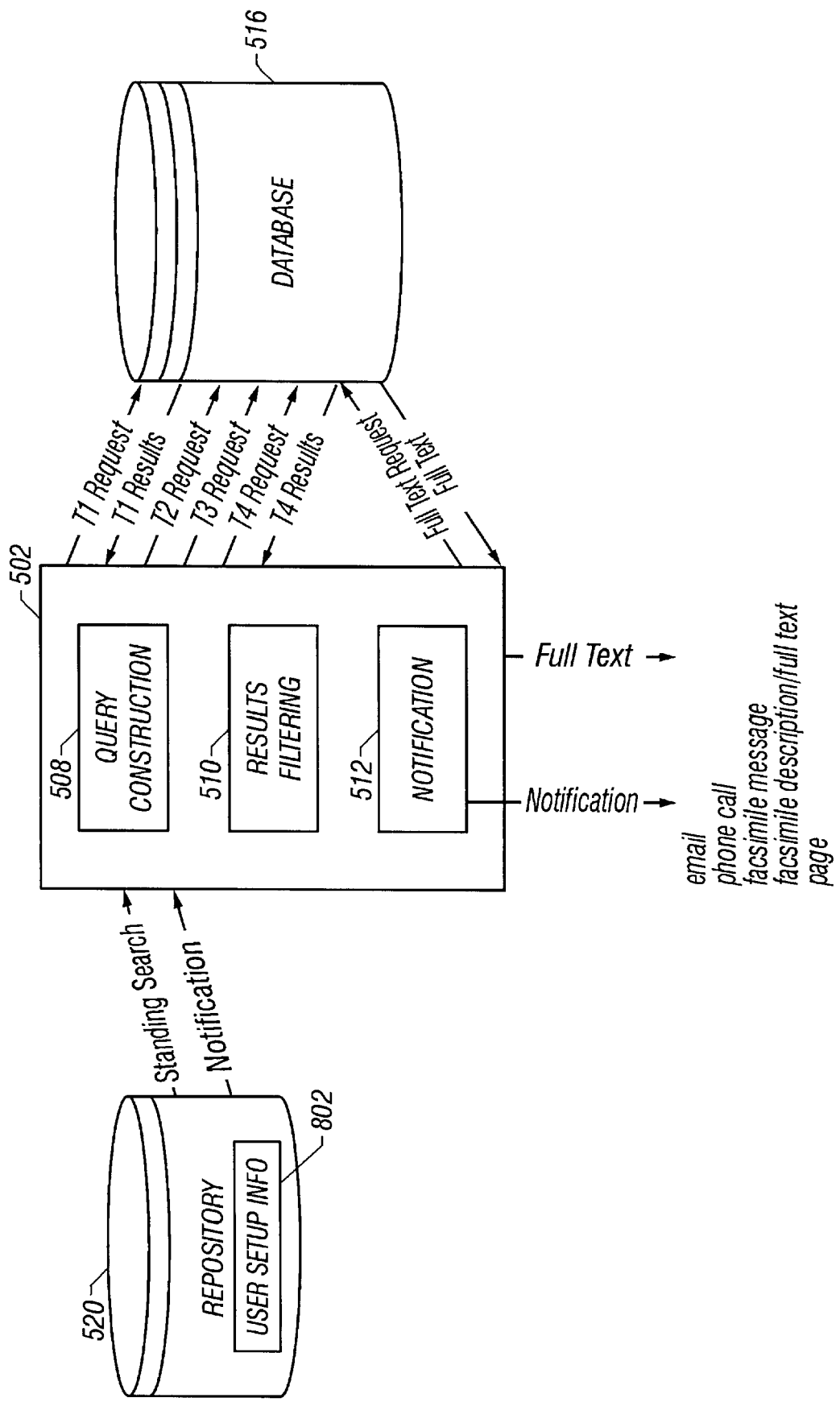
FIG. 8 illustrates an overview of a standing search according to an embodiment of the invention.

FIG. 8 illustrates an overview of a standing search according to an embodiment of the invention. Repository 520 is accessed to retrieve the standing search information from user setup information 802. The standing search information is used in query construction 508 to generate a query. Periodically, the query is sent to database 516. For example, a search is sent at times $T_1$, $T_2$, $T_3$, $T_4$, etc. At time $T_1$, the search requests literature from Dec. 1, 1998 to the current time. At time $T_2$, the search requests literature that became available since time $T_1$. Similarly, the searches at times $T_3$ and $T_4$ identify literature that became available since times $T_2$ and $T_3$, respectively.

In the illustration of FIG. 8, literature is found at times $T_1$ and $T_4$. The $T_1$ and $T_4$ search results are filtered using results filtering 510. If the filtered results contain articles, notification 512 notifies the user according to the manner of notification specified by the user in user setup 404. As previously described, examples of notifications include email, phone, facsimile, and/or page. The user may also be notified via a display in a computer display once the user provides a user identification. A brief or detailed description may be supplied to the user as well as the full text of an articles as requested by the user.

Figure 9A:
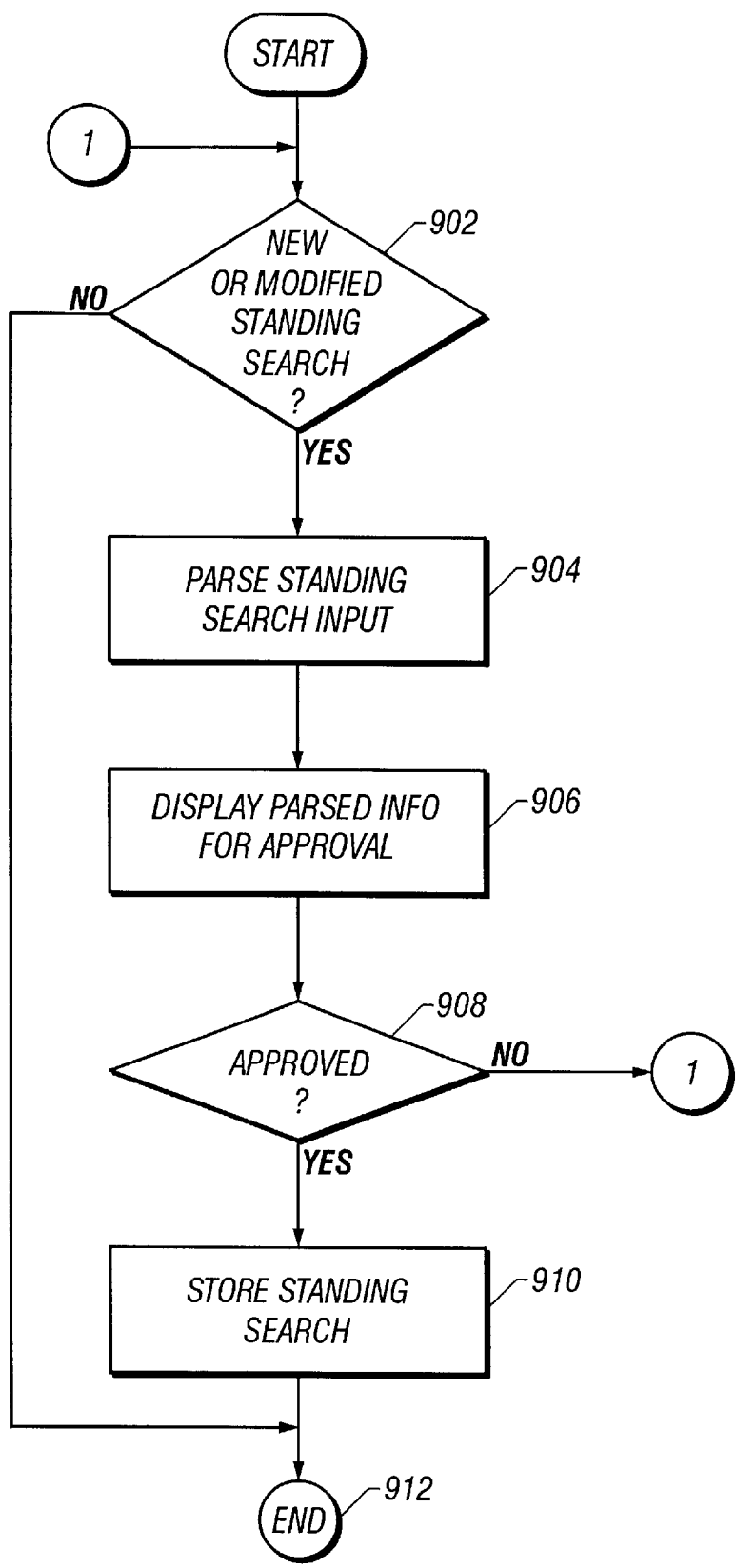
FIGS. 9A–9B provide an example of a standing search process flow according to an embodiment of the invention.
Figure 9B:
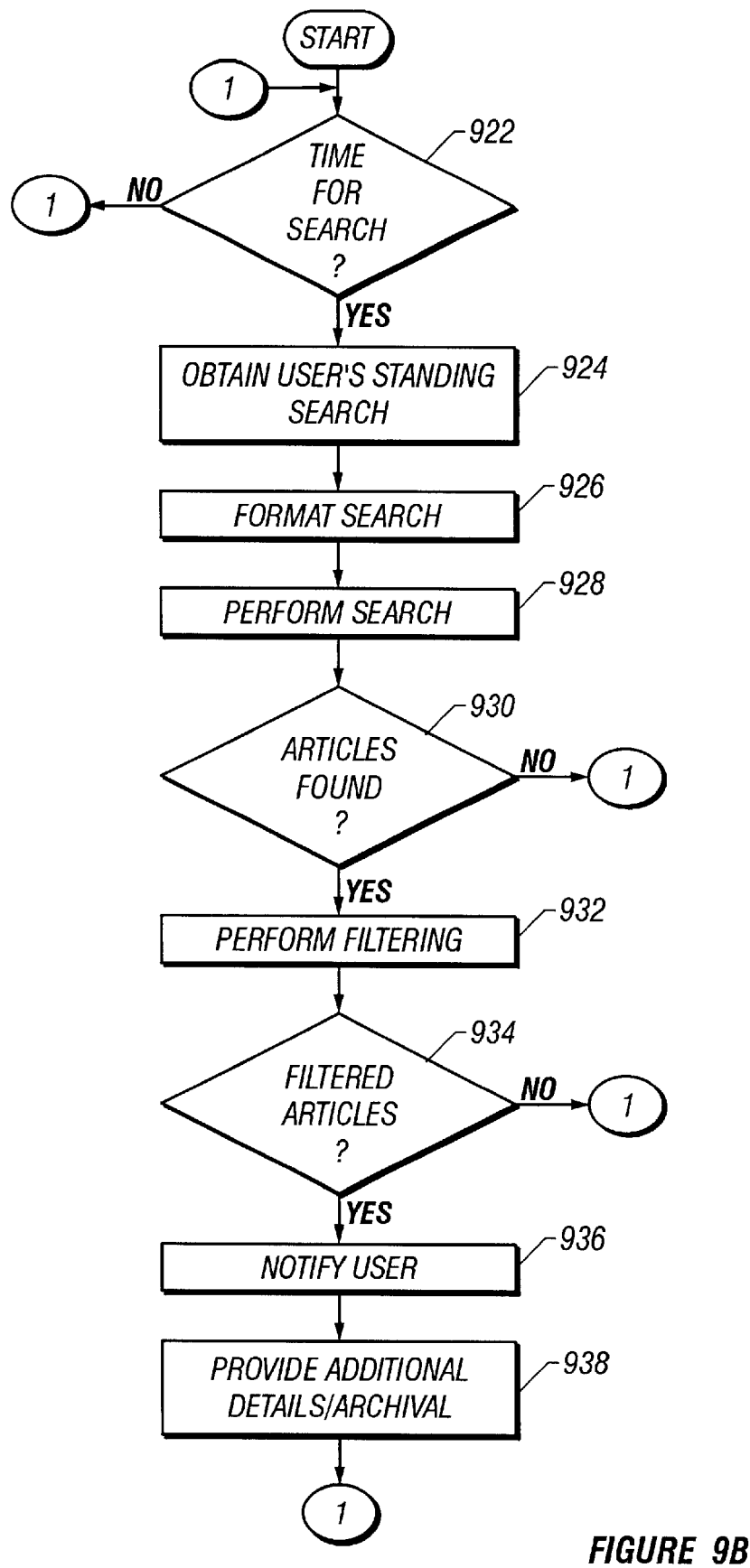

FIGS. 9A–9B provide an example of a standing search process flow according to an embodiment of the invention. Referring to FIG. 9A, an example of the standing search setup according to an embodiment of the invention. At step 902, a determination is made that the user wishes to specify a new standing search or a modification to an existing standing search. As described above, the user may enter a standing search as a natural language request according to an embodiment of the invention.

At step 904, the natural language standing search is parsed to extract search keys, time range, sources, etc. that are to be used to construct the query. At step 906, the parsed information is displayed to the user for approval. At step 908, if the parsed information is not correct, the user may modify the standing search or the parsed information. Processing continues at step 902 to handle the modifications.

If the parsed information is approved at step 908, processing continues at step 910 to store the standing search and/or parsed information in the user's setup information. Processing ends at step 912.

Periodically, a standing search is used to search database 516. FIG. 9B provides an example of a standing search according to one or more embodiments of the invention. At step 922, a determination is made whether it is time for a standing search. If so, processing continues at step 924 to obtain the standing search from the user's setup information. At step 926, the standing search is used to format the search which may include data conversion such as previously described (e.g., diagnosis and age conversions).

At step 928, the searched is performed using database 516. At step 930, a determination is made whether any literature was found in the search. If not, processing continues at step 922 to await the initiation of the standing search. If literature was found in the search, processing continues at step 932 to perform any filtering of the search results. At step 934, a determination is made whether the filtered search results contains any literature. If not processing continues at step 922 to await the next standing search.

If the filtered search results contain literature, the user is notified at step 936. The manner and content of the notification are specified in the user's setup information. At step 938, additional information not contained in the notification may be supplied to the user as well as perform archival functions. Processing continues at step 922 to await the next standing search.

Ad Hoc Access

At any time, a user may request an ad hoc search. For example, a physician may request a search while viewing a patient's chart. If the user initiates an ad hoc search, the user is given the option to modify the setup information to customize the ad hoc search. The user may modify the setup information for the ad hoc search only or may make the modifications permanent.

Figure 10:
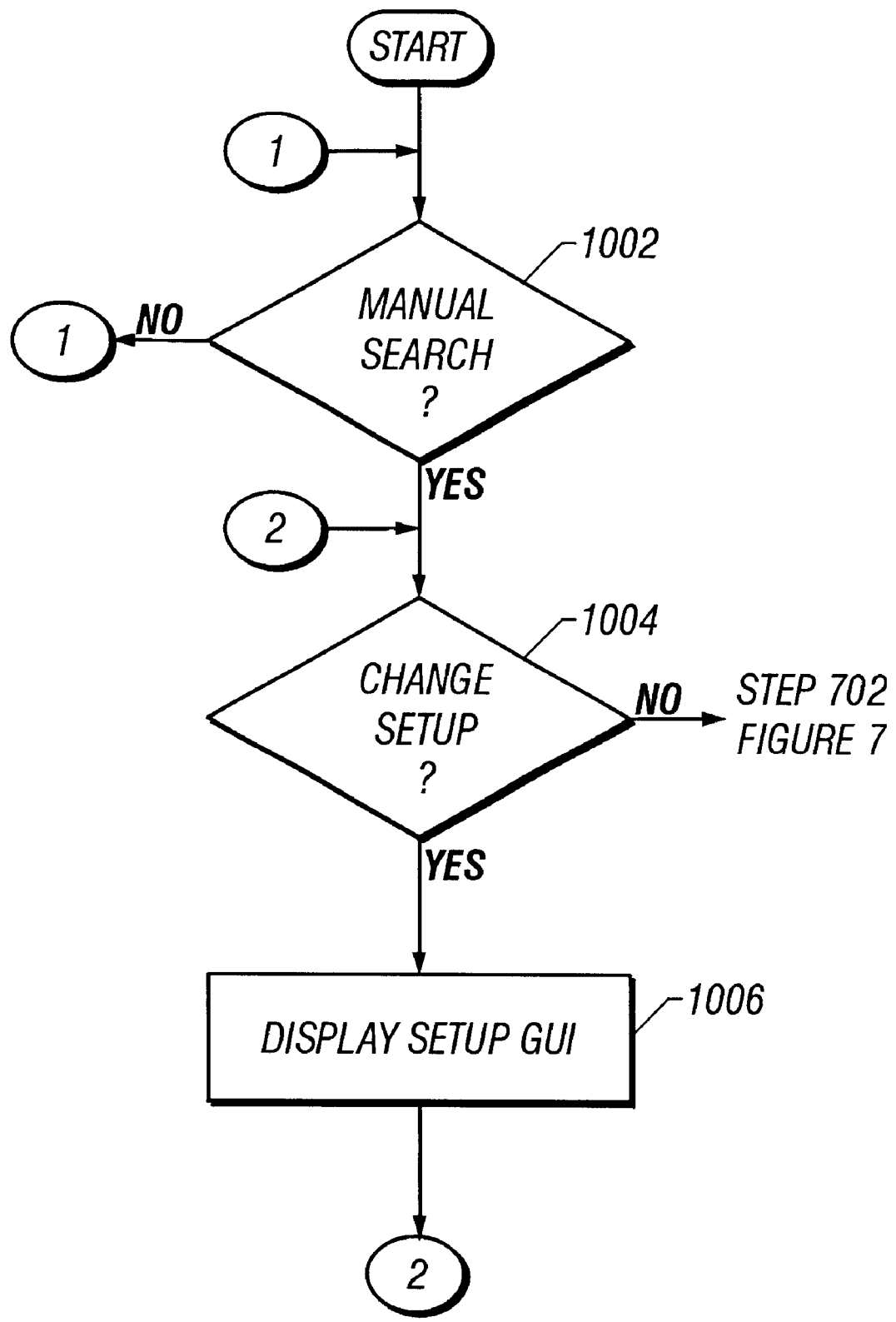
FIG. 10 provides an example of an ad hoc search process flow according to an embodiment of the invention.

Referring to FIG. 5, a user may initiate a search by selecting button 522. FIG. 10 provides an example of an ad hoc search process flow according to an embodiment of the invention. At step 1002, a determination is made whether button 522 is selected. If so, processing continues at step 1004 to ask the user whether or not the user wishes to modify setup information. If so, process continues at step 1006 to enter user setup 404 to allow the user to modify setup information. Modifications may be made permanently or for the duration of the manual search, for example. If it is determined at step 1004 that the user does not wish to modify (or has made all of the desired modifications to) the setup information, processing continues at step 702 of FIG. 7 to process the ad hoc search request.

Archival

Figure 11:
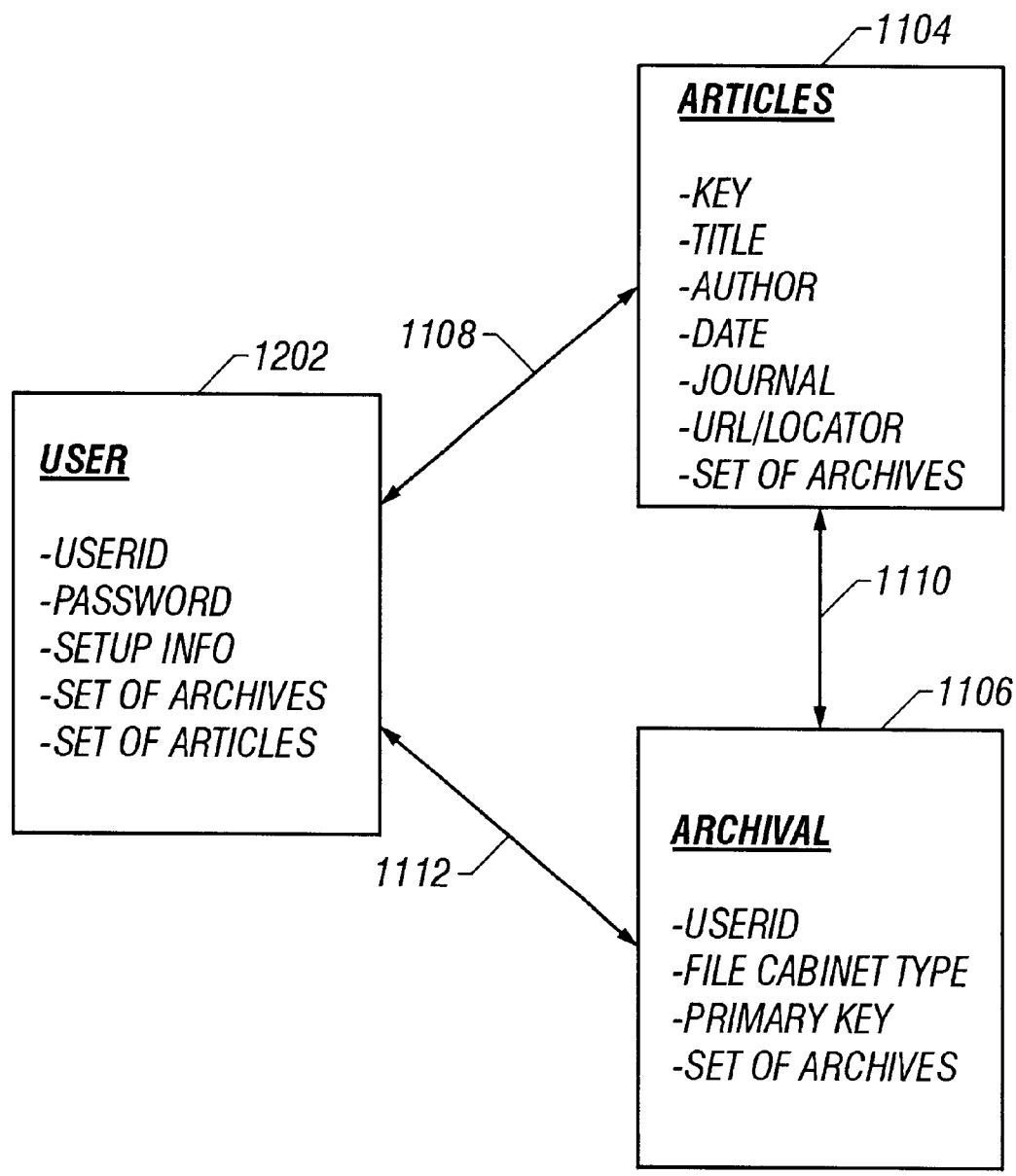
FIG. 11 provides an example of repository information and their inter-relationships according to an embodiment of the invention.

Embodiments of the invention allow a user to save information about articles found in a search in repository 520, for example. An electronic filing cabinet is provided that saves an article in one or more archival categories. For example, articles may be categorized based on the organ system to which the article is related or by related diagnosis, by bibliographic information, or other user-defined categories. FIG. 11 provides an example of repository information and their inter-relationships between a user (e.g., physician, the articles found during a search, and archived articles) according to an embodiment of the invention.

Blocks 1102, 1104 and 1106 represent examples of tables (e.g., relational database tables) and the information fields or columns that comprise records that are stored in a table. Relationships 1108, 1110 and 1112 represent examples of relationships between the tables.

User table 1102 contains information associated with a user. A userid field (e.g., the unique user identification specified in user setup 404) uniquely identifies each record in user table 1102. Other user information such as password and setup information may be stored in the user record. Articles table 1104 contains information about articles found in searches. A record in articles table 1104 may contain a unique key to uniquely identify a record and the article's title, author, publication date, journal, locator (e.g., URL) and status.

Archival table 1106 identifies the storage categories (or file cabinets) in which articles, or searches, may be stored. A file cabinet type identifies the type of archival category (e.g., organ system, diagnosis, bibliographic, user-defined). A file cabinet is used by a given user to store information. Thus, an archival record identifies the user to whom the file cabinet belongs.

Each of tables 1102, 1104 and 1106 further include sets of information that correspond to a relationship between two tables. For example, a user record may be related to none or more articles (e.g., a set of articles) via relationship 1108. Relationship 1108 is a many to many relationship. That is, none or more users may be related to none or more articles. For example, the same article may have been found for more than one user. Conversely, multiple articles may have been found for a user as a result of one or more search(es).

Relationship 1112 illustrates that a user may have more than one archival category (e.g., file cabinet) in which articles may be stored. Further, none or more users may use the same archival category to store articles. Relationship 1110 indicates that a file cabinet may contain none or more articles. Conversely, the same article may be stored in none or more archival categories.

When a search is conducted for a user, information associated with articles that are found during the search may be stored in articles table 1104. An association is made between the article(s) and the user for whom the search was conducted. Thus, it is possible to determine which articles have already been found for a given user. If the user decides to store an article, the article's record in articles table 1104 is related to the archival record associated with the category in which the user wishes to store the article.

The tables and relationships illustrated in FIG. 11 are illustrations of that may be used to store user and search information. Other tables and relationships may be used to supplement or replace those shown in FIG. 11.

Search Optimizations

Record link searches may be performed (and a connection established to database 516) when a user accesses a chart. Alternatively, a record link search may be kept up-to-date as new publications become available independent of when a user accesses the chart. The results may be stored in repository 520 for future use. Thus, when the user accesses the chart, there is no need to access database 516. This may reduce the amount of time needed to notify the user.

Further, the same search may be performed for multiple doctors. Where for example, approximately 20 percent of all the known diagnoses account for 90 percent of the actual diagnoses, it is possible that repeated searches may be performed. For example, if both Dr. Smith and Dr. Jones are treating two different individuals for asthma, it may be possible to combine these searches such that the results of one search may be used for both. Searches may be combined where the search criteria is similar, for example. Thereafter, a single updating search may be performed as a more recent publication becomes available (e.g., when the next issue of the New England Journal of Medicine is published).

Presentation Optimizations

In one or more embodiments of the invention, search results contained in display 606 may be ranked or ordered based on an interest in the article exhibited by users perusing previous search results that contain the article. For example, embodiments of the invention order search results putting the most popular articles first (e.g., those articles most frequently retrieved and/or saved adjusted by age of article).

Embodiments of the invention monitor the results of a search and the choices that are made by a user. The choices that are made by one user in viewing search results may be used to optimize the presentation of a subsequent search that includes the some or all of the previous search's search results. For example, assume that a prior search includes five articles, and when one user views the search results the user decides to keep (i.e., save) article one and article five. However, the user was not interested in articles two, three and four. The user's interest in articles one and five as well as the user's disinterest in the other three articles in the search is noted and retained. Other user's preferences with respect to search results may be similarly collected.

A future user's interest in a given article may be predicted given the interest shown by user's in previous searches. In embodiments of the invention, the prediction may be used to determine a presentation order for articles in a subsequent search. As indicated above, the presentation order may be adjusted based on the age of the articles in the search results.

Embodiment of Computer Execution Environment (Hardware)

Figure 12:
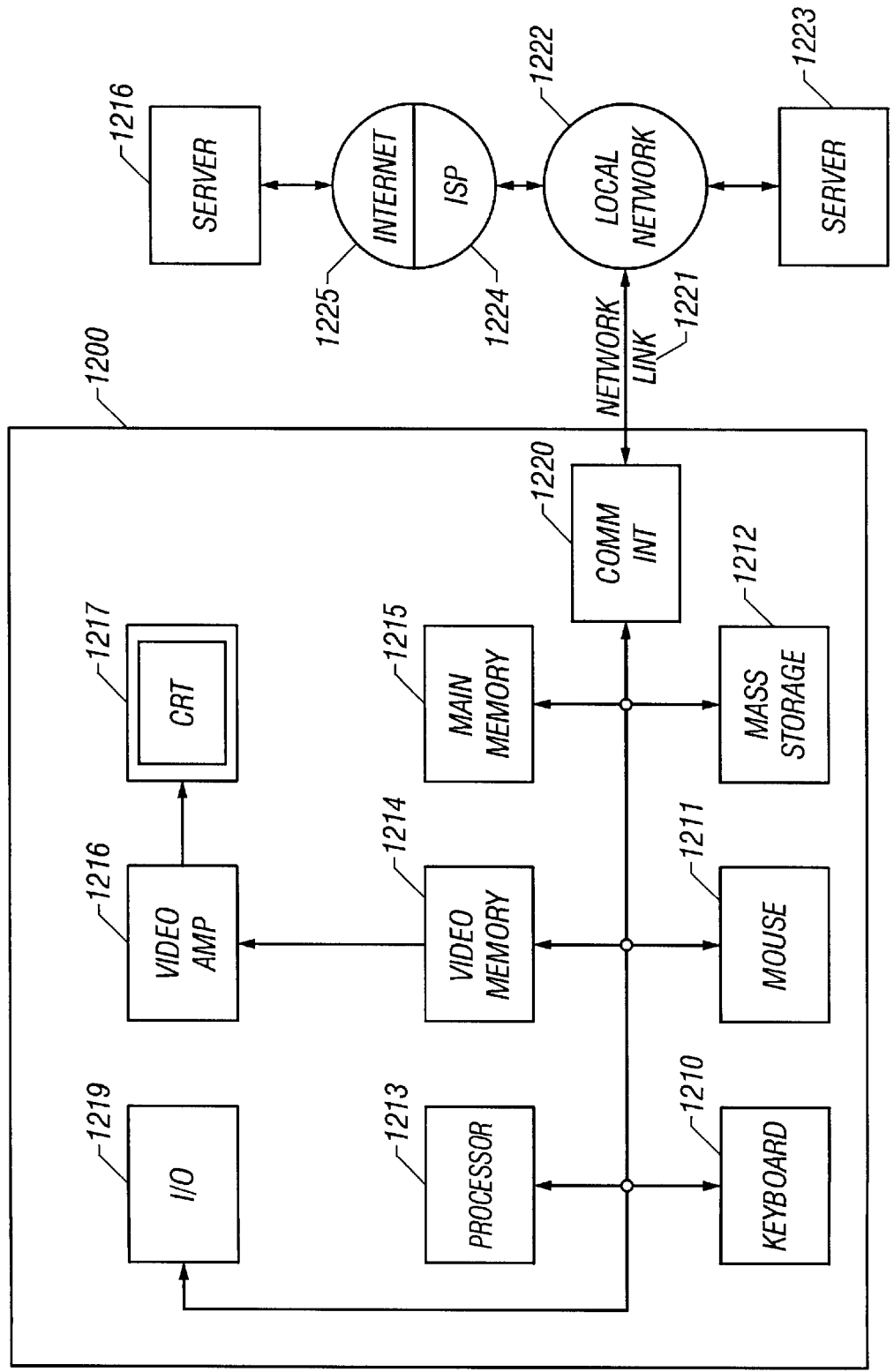
FIG. 12 is a block diagram of one embodiment of a computer system capable of providing a suitable execution environment for an embodiment of the invention.

An embodiment of the invention can be implemented as computer software in the form of computer readable code executed on a general purpose computer such as computer 1200 illustrated in FIG. 12, or in the form of bytecode class files executable within a Java runtime environment running on such a computer. A keyboard 1210 and mouse 1211 are coupled to a bi-directional system bus 1218. The keyboard and mouse are for introducing user input to the computer system and communicating that user input to processor 1213. Other suitable input devices may be used in addition to, or in place of, the mouse 1211 and keyboard 1210. I/O (input/output) unit 1219 coupled to bi-directional system bus 1218 represents such I/O elements as a printer, A/V (audio/video) I/O, etc.

Computer 1200 includes a video memory 1214, main memory 1215 and mass storage 1212, all coupled to bi-directional system bus 1218 along with keyboard 1210, mouse 1211 and processor 1213. The mass storage 1212 may include both fixed and removable media, such as magnetic, optical or magnetic optical storage systems or any other available mass storage technology. Bus 1218 may contain, for example, thirty-two address lines for addressing video memory 1214 or main memory 1215. The system bus 1218 also includes, for example, a 32-bit data bus for transferring data between and among the components, such as processor 1213, main memory 1215, video memory 1214 and mass storage 1212. Alternatively, multiplex data/address lines may be used instead of separate data and address lines.

In one embodiment of the invention, the processor 1213 is a microprocessor manufactured by Motorola, such as the 680X0 processor or a microprocessor manufactured by Intel, such as the 80X86, or Pentium processor, or a SPARC microprocessor from Sun Microsystems, Inc. However, any other suitable microprocessor or microcomputer may be utilized. Main memory 1215 is comprised of dynamic random access memory (DRAM). Video memory 1214 is a dual-ported video random access memory. One port of the video memory 1214 is coupled to video amplifier 1216. The video amplifier 1216 is used to drive the cathode ray tube (CRT) raster monitor 1217. Video amplifier 1216 is well known in the art and may be implemented by any suitable apparatus. This circuitry converts pixel data stored in video memory 1214 to a raster signal suitable for use by monitor 1217. Monitor 1217 is a type of monitor suitable for displaying graphic images. Alternatively, the video memory could be used to drive a flat panel or liquid crystal display (LCD), or any other suitable data presentation device.

Computer 1200 may also include a communication interface 1220 coupled to bus 1218. Communication interface 1220 provides a two-way data communication coupling via a network link 1221 to a local network 1222. For example, if communication interface 1220 is an integrated services digital network (ISDN) card or a modem, communication interface 1220 provides a data communication connection to the corresponding type of telephone line, which comprises part of network link 1221. If communication interface 1220 is a local area network (LAN) card, communication interface 1220 provides a data communication connection via network link 1221 to a compatible LAN. Communication interface 1220 could also be a cable modem or wireless interface. In any such implementation, communication interface 1220 sends and receives electrical, electromagnetic or optical signals which carry digital data streams representing various types of information.

Network link 1221 typically provides data communication through one or more networks to other data devices. For example, network link 1221 may provide a connection through local network 1222 to local server computer 1223 or to data equipment operated by an Internet Service Provider (ISP) 1224. ISP 1224 in turn provides data communication services through the world wide packet data communication network now commonly referred to as the "Internet" 1225. Local network 1222 and Internet 1225 both use electrical, electromagnetic or optical signals which carry digital data streams. The signals through the various networks and the signals on network link 1221 and through communication interface 1220, which carry the digital data to and from computer 1200, are exemplary forms of carrier waves transporting the information.

Computer 1200 can send messages and receive data, including program code, through the network(s), network link 1221, and communication interface 1220. In the Internet example, remote server computer 1226 might transmit a requested code for an application program through Internet 1225, ISP 1224, local network 1222 and communication interface 1220.

The received code may be executed by processor 1213 as it is received, and/or stored in mass storage 1212, or other non-volatile storage for later execution. In this manner, computer 1200 may obtain application code in the form of a carrier wave. In accordance with an embodiment of the invention, examples of such downloaded applications include a method and apparatus for accessing information described herein.

Application code may be embodied in any form of computer program product. A computer program product comprises a medium configured to store or transport computer readable code or data, or in which computer readable code or data may be embedded. Some examples of computer program products are CD-ROM disks, ROM cards, floppy disks, magnetic tapes, computer hard drives, servers on a network, and carrier waves.

The computer systems described above are for purposes of example only. An embodiment of the invention may be implemented in any type of computer system or programming or processing environment, including embedded devices (e.g., web phones, etc.) and "thin" client processing environments (e.g., network computers (NC's), etc.) that support a virtual machine.

Thus, a method and apparatus for accessing information has been described in conjunction with one or more specific embodiments. The invention is defined by the claims and their full scope of equivalents.

What is claimed is:

1. In a computer system, a method of providing professional service client information comprising:
   automatically obtaining data from at least one case data repository;
   using said data from said at least one case data repository to generate a report about a professional service client associated with a current user, said report comprising at least one field;
   automatically formulating a search query when said current user opens a user interface associated with said report, said search query comprising said at least one field from said report;
   obtaining results by using said search query to perform a search of at least one data source;
   obtaining previous user retrieval information and previous user profile information;
   evaluating said previous user retrieval information and said previous user profile information to determine an interest level associated with said current user; and
   ordering said results according to said interest level in said data and presenting said results to said current user.

2. The method of claim 1 further comprising:
   filtering said results to eliminate data included in a previous search.

3. The method of claim 1 wherein said search query is formulated by obtaining information from said report and from said current user.

4. The method of claim 3 wherein said search query is automatically formulated when a current user opens a record management system.

5. The method of claim 1 wherein said case data repository comprises a case history associated with said professional service client.

6. The method of claim 5 wherein said case history associated with said professional service client comprises information about past visits to said current user.

7. The method of claim 1 wherein said evaluating step is performed when a first scope of professional practice associated with a current user profile for said current user resembles a second scope of professional practice associated with at least one said previous user profile.

8. The method of claim 1 wherein said evaluating step is performed when said search query has attributes in common with a previous search query.

9. The method of claim 1 further comprising:
   displaying said results to a current user.

10. The method of claim 1 further comprising:
displaying an alert icon when said results changes.

11. In a computer system, a method of providing information comprising:
obtaining a current user profile that differs from a previous user profile;
automatically formulating a search query when a current user having said current user profile opens a user interface, said search query comprising at least one field;
automatically obtaining results, said results comprising literature obtained using said search query to perform a search of at least one literature source;
determining if said current user profile has attributes in common with said previous user profile associated with said at least one of a plurality of previous users, each of said previous user profile comprising a previous user retrieval pattern;
determining an interest level associated with said current user in said literature by evaluating said previous user retrieval patterns where at least one of said previous user retrieval patterns is not a current user retrieval pattern;
ranking said results according to said interest level in said literature; and
presenting said results to said current user.

12. The method of claim 11 further comprising:
filtering said results to eliminate literature included in a previous search.

13. The method of claim 11 wherein said user retrieval pattern identifies literature stored by said previous user.

14. The method of claim 11 wherein said search query is formulated by obtaining information from said at least one field where said at least one field comprises data associated with a professional service client stored in a database.

15. The method of claim 14 wherein said search query is automatically formulated when said current user opens a case history report associated with a record management system for managing professional service client information.

16. The method of claim 14 wherein said at least one field of said database comprises historical data associated with said professional service client.

17. The method of claim 16 wherein said professional service client information comprises information obtained from a professional service client record.

18. The method of claim 11 further comprising:
displaying an alert icon when said results change.

19. The method of claim 11 further comprising notifying said current user when said results are obtained.

20. In a computer system, a method for providing information comprising:
automatically generating a search query when a current user opens a user interface;
obtaining search results comprising literature references by using said search query to search a plurality of literature sources;
determining at least one previous user interest level in said results, where said at least one previous user interest level is associated with at least one previous user that is not said current user;
ordering said results based on said at least one previous user interest level; and
presenting said ordered results to said current user that is not said at least one previous user.

21. The method of claim 20 wherein said at least one previous user interest level is based on the number of said at least one previous users that obtained said literature contained in said search results.

22. The method of claim 20 wherein said at least one previous user interest level is based on the number of said at least one previous users that saved said literature contained in said results.

23. The method of claim 20 wherein said search query is automatically formulated by obtaining information from a database having fields.

24. The method of claim 23 wherein said database comprises computerized records and said fields comprise data associated with at least one client.

25. The method of claim 23 wherein said fields comprise data associating a specialty with said current user.

26. The method of claim 25 wherein said specialty defines a scope of professional practice.

27. The method of claim 26 wherein said results obtains said plurality of literature sources based on said specialty of said current user.

28. The method of claim 24 wherein said data associated with said at least one matter comprises patient data.

29. The method of claim 28 wherein said patient data comprises diagnostic information, age, and gender information.

30. The method of claim 29 wherein said patient data further comprises data associating a specialty with said current user.

31. The method of claim 24 wherein said search query is formulated when said current user opens said user interface associated with said computerized records.

32. In a computer system, a method for providing information comprising:
obtaining search results comprising literature references by using a search query to perform a search of a plurality of literature sources, wherein said search query is automatically generated when a current user opens a user interface;
determining at least one previous user interest level in said literature, wherein said at least one previous user interest level is based on the number of said at least one previous users who obtained said literature from said search results;
ordering said results based on said at least one previous user interest level; and
presenting said ordered results to a current user having a specialty associated with said at least one previous user.

33. In a computer system, a method for providing information comprising:
automatically generating a search query comprising data obtained from a computerized records system having fields when a user interface is opened;
obtaining search results comprising literature references by using a search query to perform a search of a plurality of literature sources;
determining at least one previous user interest level in said results, wherein said at least one previous user interest level is based on the number of said at least one previous users that obtained said literature from said search results;
ordering said results based on said at least one previous users interest level and a similarity between a specialty of a current user and a specialty of said at least one previous user; and
presenting said results to said current user having a specialty associated with said at least one previous user.

34. The method of claim 33 wherein said at least one previous user interest level is based on the frequency with which said at least one previous user saved said literature from said results.

35. The method of claim 33 wherein said fields comprise data associated with at least one matter.

36. The method of claim 35 wherein said data associated with said at least one individual comprises patient data.

37. The method of claim 33 wherein said specialty defines an scope of professional practice.

38. The method of claim 33 wherein said search query is formulated when said current user opens said computerized records.

39. In a computer system, a method of providing professional service client information comprising:

obtaining a current user profile associated with a current user, said current user profile comprising a current user specialty;

obtaining data from at least one case data repository when said current user opens a user interface for managing information about a professional service client;

generating a report comprising at least one field, said at least one field having case history information about said professional service client;

automatically formulating a search query when said current user opens a user interface associated with managing said case history information, said search query comprising said at least one field from said report;

obtaining search results comprising literature references by using said search query to perform a search of at least one literature data source; and presenting said search results to said current user.

40. The method of claim 39 wherein said obtaining said search results further comprises:

obtaining retrieval information associated with a plurality of previous user profiles where at least one of said plurality of previous user profiles is not representative of said current user profile, said retrieval information identifying literature obtained by a plurality of previous users each having at least one of said plurality of previous user profiles;

determining an interest level in said search results, where said interest level is based on said retrieval information associated with said plurality of previous user profiles and a similarity between said current user specialty and at least one previous user specialty; and arranging said search results based on said interest level.

* * * * *